United States Patent

Salam

[11] Patent Number: 6,013,079
[45] Date of Patent: Jan. 11, 2000

[54] AEROSOLIZED BONE DUST AND BODY FLUIDS EXTRACTION SYSTEM FOR A BONE CUTTING SAW

[76] Inventor: Abdul Salam, P.O. Box 6847, Laguna Niguel, Calif. 92607-6847

[21] Appl. No.: 09/146,186

[22] Filed: Sep. 1, 1998

[51] Int. Cl.$^7$ .................................................. A61B 17/14
[52] U.S. Cl. ................................ 606/82; 606/79; 606/176
[58] Field of Search ................................ 606/79, 82, 176; 30/390, 276

[56] References Cited

U.S. PATENT DOCUMENTS

| | | |
|---|---|---|
| 2,369,925 | 2/1945 | Smith . |
| 2,742,974 | 4/1956 | Landgraf . |
| 3,896,783 | 7/1975 | Manning . |
| 4,008,720 | 2/1977 | Brinckmann et al. . |
| 4,022,182 | 5/1977 | Lenkevich . |
| 4,411,067 | 10/1983 | Kirk . |
| 5,074,044 | 12/1991 | Duncan et al. . |
| 5,122,142 | 6/1992 | Pascaloff . |

*Primary Examiner*—Michael Buiz
*Assistant Examiner*—Daphne Shai
*Attorney, Agent, or Firm*—James G. O'Neill

[57] ABSTRACT

An improved aerosolized bone dust and body fluid extraction system for an oscillating or reciprocating saw includes a water line, control valve and inlet nozzle to spray water into the area in and around an oscillating or reciprocating saw blade and an exhaust manifold to aid in the removal of aerosolized bone dust and body fluids during cutting. Additionally, the end of the housing holding the oscillating or reciprocating saw blade may be provided with a vented elongated shaped skirt member for guarding against splatter of aerosolized bone dust and body fluids and for acting against the surface being cut by the saw blade so as to improve the efficiency of the exhaust system and prevent the spread of aerosolized bone dust and body fluids to thereby prevent the spread of toxic materials and/or communicable diseases.

10 Claims, 1 Drawing Sheet

AEROSOLIZED BONE DUST AND BODY FLUIDS EXTRACTION SYSTEM FOR A BONE CUTTING SAW

BACKGROUND OF THE INVENTION

1. Field of the Invention

This invention relates generally to dust and fluid extraction systems, and, more particularly, to an aerosolized bone dust and body fluid extraction system for a bone cutting saw.

2. Description of Related Art

It is well known that when cutting bones in a body, such as the skull of a body during an autopsy, that aerosolized bone dust and body fluid particulates are dispersed into the air. Because of the health risks and other problems arising from such aerosolized bone dust and body fluids, vacuum exhaust systems are required on saws being used by pathologists, physicians, surgeons, veterinarians or technicians preforming such cuttings. However, with the increase in toxicity levels within a person's body, and the rising fear of contracting diseases from bodies, there exists a need to prevent any and all aerosolized bone dust and body fluids created during a cutting and/or an autopsy procedure from escaping. However, known devices are not efficient enough to enable all such aerosolized particles to be captured, and, therefore, some serious events have occurred.

Many prior art cutting and drilling devices are known, but such devices are not adaptable for and cannot be used when cutting bone in a human or animal in all situations, in a safe and secure manner. For example, such known devices include saws for cutting wood, concrete, or other similar types of materials, and may include exhaust systems. One such device is shown in U.S. Pat. No. 4,022,182 to Lenkevich which discloses a housing unit for a circular saw wherein dust and debris are removed by suction. Housing 12, which surrounds the cutting blade 50, is provided with a discharge tube 70 for coupling to a remotely located suction source through the hose 72. The suction source is a heavy duty industrial vacuum The housing 12 is also provided with a nozzle 60 for injection of a fluid to cool and clean the blade. The dust and other particles generated by the cutting operation are carried along with the water into the discharge tube by virtue of the suction applied thereto;

Another prior art device is shown in U.S. Pat. No. 2,742,974 to Landgraf which discloses a method and system for cleaning air laden with an oil mist. In this system, a fluid (oil) is applied to the workpiece, at its point of contact, with the machine tool, in the form of a fine spray. A suction source 16 creates a low pressure within the conduit 11 for drawing the oil mist and particulates away from the machine tool, and to an electrostatic precipitator 12;

U.S. Pat. No. 3,896,783 to Manning discloses a machine tool for cutting concrete. The cutting apparatus 10 includes a fluid applicator assembly 18 which is connected to a fluid source 20, for applying fluid to a portion of the cutting blade 14. The applied fluid serves multiple purposes, including cooling and lubricating the cutting blade 14;

U.S. Pat. No. 2,369,925 to Smith discloses a surgical instrument for cutting bone. The cutter 1 is provided with a circular pump housing 18 for creating a rearwardly directed suction for removing the instrument's cuttings and discharging such cuttings through the port 23 of the discharge nozzle 24;

U.S. Pat. No. 4,008,720 to Brinckmann et al. discloses an oscillating bone saw blade 4 having a plurality of readily extending channels 6, 7 and 8 for carrying a cooling and lubricating fluid therethrough; and U.S. Pat. No. 5,074,044 to Duncan et al. discloses a dust disposal attachment for use with power driven saws. The suction housing 40 encloses an impeller 38 which is driven by the tool's rotary shaft 18 from withdrawing dust and debris through the opening 32 formed in the blade guard 22. The dust and debris, which is removed from the blade guard, is discharged through the port 46 to the hose 120, which may be connected to a dust collection chamber.

While the exhaust and injection systems of these known devices provide improvements in the art and overcome many of the problems encountered when cutting wood and/or concrete, they are not readily applicable to oscillating or reciprocating saws for cutting mammal bones, and/or cannot be adapted to meet todays' more stringent health and safety requirements. Moreover, they would not prevent splatter, or remove all aerosolized particulates. Therefore, there still exists a need in the art for an improved system for use with an oscillating or reciprocating bone cutting saw, to remove substantially all of the aerosolized bone dust and body fluids created during the cutting of animal or human bones.

SUMMARY OF THE INVENTION

Accordingly, it is a general object of the present invention to provide an improved fluid extraction system. It is a particular object of the present invention to provide an improved combination bone dust and body fluid extraction system. It is a still more particular object of the present invention to provide an improved bone dust and body fluid extraction system for use with an oscillating or reciprocating bone cutting saw. It is yet a more particular object of the present invention to provide an improved aerosolized bone dust and body fluid extraction system having a splatter guard and sealing member which may be used to ensure that substantially all of the airborne particles created during the cutting of mammal bones by an oscillating or reciprocating saw are extracted.

In accordance with one aspect of the present invention, there is provided a combination aerosolized bone dust and body fluid extraction system for an oscillating or reciprocating bone cutting saw, having a housing with an exhaust manifold connected to an exhaust tube, an inlet for fluid having a control valve in a connecting line; and a resilient splatter guard and sealing system to enable substantially all airborne particles to be extracted during a cutting operation with the oscillating or reciprocating saw.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, in which:

DESCRIPTION OF THE PREFERRED EMBODIMENTS

Figure 1:
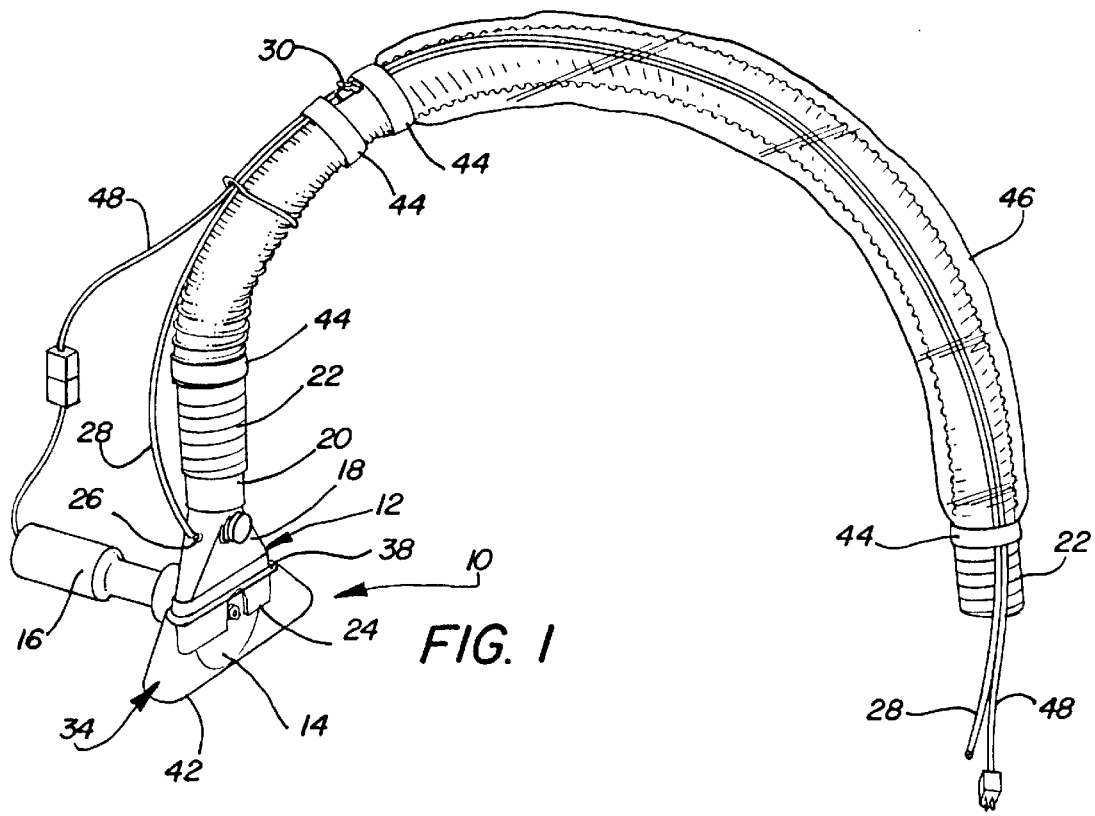
FIG. 1 is a perspective view showing a preferred embodiment of an aerosolized bone dust and body fluid extraction system of the present invention attached to an oscillating or reciprocating bone cutting saw, having a unique splatter guard and sealing skirt connected thereto, at the outer end, surrounding an oscillating or reciprocating saw blade.
Figure 2:
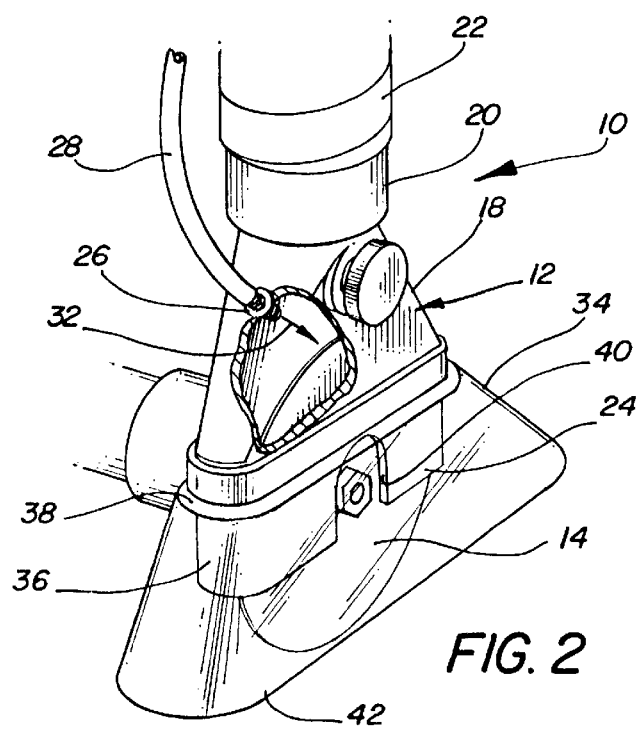
FIG. 2 is an enlarged perspective view, partially in cross section, showing further details of the improved system of the present invention.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide for an improved aerosolized bone dust and body fluid extraction system, generally indicated by the numeral 10, for use with an oscillating or reciprocating saw 12 when cutting mammal (animal or human) bone, for example, during an autopsy or operation.

As shown in the drawing figures, the present invention includes a known type of oscillating or reciprocating bone cutting saw blade 14, driven by an electric or pneumatic motor 16 and held in a housing 18. The housing 18 includes an upper end having an exhaust manifold 20 connected to an exhaust tubing 22. The tubing 22 is connected to an industrial vacuum source, not shown, so as to extract dust and other particulates generated by the bone cutting saw during use. Many problems have occurred when cutting bone in an animal or human body using known oscillating or reciprocating saw blades held within known housings. In particular, aerosolized bone dust and body fluids have been known to splatter about and/or escape from under a lower portion 24 and one or more openings 40 in the housing 18, and to not be extracted through the exhaust manifold 20 and exhaust tubing 22. Therefore, the present system has been developed to include a fluid inlet 26, such as a nozzle, or the like, secured in an opening, drilled or otherwise formed, in the housing 18. A fluid line 28, such as a water line, is connected to the inlet 26 and one or more valves 30 are provided in the line 28 to control the flow of water therethrough. The line 28 is, in turn, attached at its outer end to a fluid source, such as a water supply, not shown, in a known manner. Therefore, upon opening of the valve 30, water or other fluid flows through the line 28 and through the inlet 26, so as to be dispersed or sprayed, in the direction of arrow 32, in and around the saw blade 14. The fluid spray captures airborne bone dust and body fluids within the interior of housing 18 to aid in exhausting such entrapped particles through the manifold 20 and tubing 22. A decontaminant solution can be pumped to the extraction head 18, to kill bacteria upon contact at the source.

Additionally, a shaped skirt member 34, which acts as a splatter guard and sealing element, may be attached around a substantially oval lower portion 36 of the housing 18. The splatter guard and sealing element 34 is sized and dimensioned so that the top portion 38 thereof is held on the oval portion 36, and may include a venting means, such as a screen over an opening 40, so as to prevent most aerosolized bone dust or fluids from leaking past the end 24, or through the opening 40. Additionally, the splatter guard/securing portion 34 is preferably enlarged or flared outwardly toward the bottom thereof, so that a lower area or portion 42 is able to capture and hold any aerosolized bone dust and body fluids created around the outer diameter of the circular saw 14, within the interior of the splatter guard 34, thereby enabling all such aerosolized bone dust and body fluids to be extracted outwardly through the exhaust tubing 22.

When used, the lower end 42 of the splatter guard/sealing element 34 is preferably aligned with, or in a slightly lower plane than the outer diameter or edge of the saw blade 14, so that when the saw blade is placed against a surface, such as a bone or skull to be cut, the lower end 42 will press against the same and act as a seal to further prevent aerosolized bone dust and body fluids from escaping from within the interior area of the splatter guard and sealing element 34, except for any venting means formed therein.

Although the skirt member 34 is shown as being transparent, it is to be understood that such a skirt member could be opaque. Additionally, the splatter guard/sealing element 34 is preferably made from a resilient material, such as plastic, to enable it to flex and the end 42 to provide a seal against any rough or uneven surface which it is pressed during operation of the saw. The splatter guard/sealing element 34 may also be sized, dimensioned and formed so as to have an accordion or pleat-type element or portion and or sliding type venting means therein, which will collapse as the lower surface 42 comes into contact with and is pressed against a further surface during operation of the oscillating or reciprocating saw blade 14, and to enable a lower sealing contact to be maintained as the saw enters deeper into a bone as the saw blade cuts through the same.

As best shown in FIG. 1, the waterline 28 may be passed through a number of holding/sealing rings 44 surrounding the exhaust tubing 22. These holding rings 44 also sealingly hold thereon an elongated, outer, plastic, protective tubing 46. The holding rings 44 can also be used to hold an electric or pneumatic line 48 bringing power to the motor 16. The electric or pneumatic line for the motor and the fluid line may be released from the holding/sealing rings 44, and separately conveyed to their connections, so that these rings merely aid in aligning and holding the plastic protective tubing 46 over all or a portion of the length of the exhaust tubing 22. The plastic, protective tubing 46 protects the covered exterior of the exhaust tubing 22 from adverse conditions and elements to facilitate cleaning and to thereby prolong the life thereof.

Those skilled in the art will appreciate that the above-described preferred embodiments are subject to numerous modifications and adaptations without departing from the scope and spirit of the invention. Therefore, it is to be understood that, within the scope of the appended claims, the invention may be practiced is other than as specifically described herein.

What is claimed is:

1. A bone cutting saw having an oscillating or reciprocating bone cutting saw blade held in a housing driven by a motor, with the housing having an exhaust manifold connected to an exhaust tubing, the improvement comprising:
    a fluid line, controlled by a valve member, connected to a nozzle held in an opening in the housing to spray a fluid into the housing; and
    a shaped skirt, attached to a lower portion of the housing, around the oscillating or reciprocating saw blade to prevent splatter from the oscillating or reciprocating saw blade, and to aid in capturing aerosolized bone dust and body fluids therein.

2. The bone cutting saw of claim 1 wherein the shaped skirt is made from a resilient material.

3. The bone cutting saw of claim 2 wherein the shaped skirt is flared so that an upper portion thereof, connected to the housing, is smaller than a lower portion thereof.

4. The bone cutting saw of claim 3 wherein the upper portion of the flared skirt includes a venting means, and the lower portion of the shaped skirt presses against a surface being cut so as to form a seal between the lower portion and the surface being cut.

5. The bone cutting saw of claim 4, further including an elongated protective plastic tubing covering the exhaust tubing.

6. The bone cutting saw of claim 5 wherein the elongated protective plastic tubing and the fluid line are secured on the exhaust tubing by a plurality of holding rings.

7. The bone cutting saw of claim 1 wherein the shaped skirt is resilient and flared so as to have a smaller upper portion attached to the housing with a venting means therein, and a larger lower portion which may be pressed against a surface being cut to form a seal between the surface being cut and the larger lower portion.

8. A bone cutting saw having an oscillating or reciprocating saw blade held in a housing, driven by a motor, with the housing having an exhaust manifold connected to an exhaust tubing, the improvement comprising:

a fluid line, controlled by a valve member, connected to a nozzle held in an opening in the housing to spray a fluid into the housing; and a resilient shaped skirt, attached to a lower portion of the housing, around the oscillating or reciprocating saw blade, to prevent splatter from the oscillating or reciprocating saw, and to aid in capturing aerosolized bone dust and body fluids generated by the oscillating or reciprocating saw blade therein.

9. The bone cutting saw of claim 1 wherein the resilient shaped skirt is flared so that a smaller upper portion is attached to the lower portion of the housing and contains a venting means therein, and a larger lower portion extends outwardly, away from the lower portion of the housing, to a plane equivalent to an outer diameter of the oscillating or reciprocating saw blade.

10. A bone cutting saw having an oscillating or reciprocating saw blade held in a housing, driven by an electric motor, with the housing having an exhaust manifold connected to an exhaust tubing, the improvement comprising:

a fluid line, controlled by a valve member, connected to a nozzle held in an opening in the housing to spray a fluid into the housing;

a flared, resilient skirt with a small top portion having a venting means therein attached to a lower portion of the housing and a larger bottom portion surrounding the oscillating or reciprocating saw blade to prevent splatter from the oscillating or reciprocating saw, and to aid in capturing aerosolized bone dust and body fluids therein; and an elongated protective plastic tubing covering at least a portion of the exhaust tubing.

* * * * *